Figure 1:
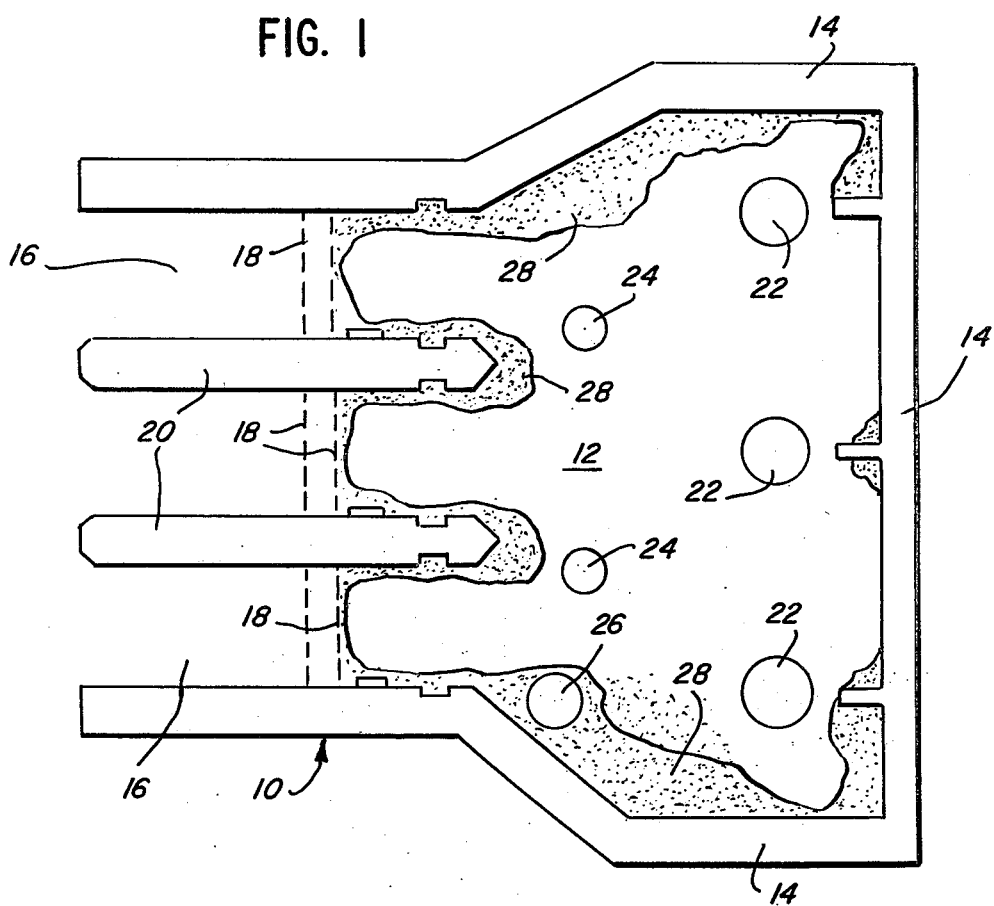

United States Patent [19]
Smithson

[11] 4,328,638
[45] May 11, 1982

[54] METHOD OF ELIMINATING MUSSELS AND THE LIKE FROM AN UNDERWATER BED

[75] Inventor: James A. Smithson, Decatur, Ill.
[73] Assignee: Illinois Power Company, Decatur, Ill.
[21] Appl. No.: 188,611
[22] Filed: Sep. 19, 1980
[51] Int. Cl.³ .............................................. A01N 23/00
[52] U.S. Cl. ...................................... 43/124; 424/162; 424/DIG. 9
[58] Field of Search .................. 43/124; 424/162, 127, 424/DIG. 9; 119/4

[56] References Cited
U.S. PATENT DOCUMENTS

| | | | |
|---|---|---|---|
| 2,731,380 | 1/1956 | Shumard | 43/124 |
| 3,105,790 | 10/1963 | Bartholomew | 424/162 X |
| 3,271,246 | 9/1966 | Howell | 43/124 |
| 4,221,782 | 9/1980 | Macphee | 424/127 |

FOREIGN PATENT DOCUMENTS
2405295 7/1975 Fed. Rep. of Germany ........ 43/124

*Primary Examiner*—Nicholas P. Godici
*Attorney, Agent, or Firm*—Charles F. Pigott, Jr.; Garrettson Ellis

[57] ABSTRACT

Mussels and related bottom dwelling creatures may be eliminated from an underwater bed by applying to the zone of at least the bottom 2 feet of water above the bed water-soluble sulfite salt such as sodium metabisulfite to substantially deplete dissolved oxygen in the zone. Thereafter, hydrogen sulfide may be directly added to the zone, being stabilized by the absence of oxygen therein the enhance the mussel kill. Thereafter, as fresh water is added to the zone, the hydrogen sulfide and residual sulfites are oxidized to relatively harmless sulfates.

29 Claims, 2 Drawing Figures

METHOD OF ELIMINATING MUSSELS AND THE LIKE FROM AN UNDERWATER BED

BACKGROUND OF THE INVENTION

Power plants and other large industrial systems utilize very large water intake cribs or screen houses which serve as a source of water for cooling systems and the like. While these structures may have a concrete floor, silt tends to collect in the corners. In some instances, clams, for example those of the variety Corbicula, flourish in the silt, having a rich supply of fresh and usually moving water which brings them food.

Unfortunately, when the clams die, their shells and even living clams have been found to be sucked into the cooling water pumps, often plugging the condenser tubes. This eventually results in a required shutdown of the facility for maintenance and removal of the clam shells from the condenser tubes.

While the problem could be solved by draining the screen house of water and removing the silt, this can be a very expensive and inconvenient technique. Furthermore, it is difficult to ultilize conventional poisons for the clams to prevent their growing to a size where the clam shells can plug the condenser tubes, since most poisons are both expensive and environmentally unsafe. A typical screen house may contain hundreds of thousands of gallons of water, so very large amounts of poison material must be placed into the water, generating undesirable environmental consequences and at great expense.

By this invention, an environmentally safe technique, utilizing inexpensive ingredients, is provided for eliminating mussels and other bottom dwelling creatures from an underwater bed, for example an underwater bed of an enclosed water intake crib or screen house for a power plant or the like.

DESCRIPTION OF THE INVENTION

In accordance with this invention, mussels and the like may be eliminated from an underwater bed by applying to the zone of at least the bottom 2 feet of water above the bed sufficient water-soluble sulfite salt, having a substantially nontoxic cation, to substantially deplete dissolved oxygen in the zone, and maintaining such conditions until the desired mussel kill is obtained. The oxygen reacts with the sulfite ion to form sulfate.

Preferably, after the oxygen has been substantially depleted in the zone, hydrogen sulfide is added to the zone to accelerate the kill. In normally oxygenated water, hydrogen sulfide is quickly oxidized to sulfurous and then sulfuric acids. However, under the substantially oxygen-depleted conditions created in the zone by the sulfite treatment, the hydrogen sulfide remains, being a highly toxic material to mussels and other bottom dwelling creatures.

Preferably, the substantially nontoxic cation is sodium, so that the sulfite salt may be sodium sulfite, or preferably sodium bisulfite or sodium metabisulfite. Other cations may be potassium, ammonium, or the like.

The sulfite salt solution may be applied through a conduit or hose directly into the zone under conditions in which currents in the water are essentially minimal.

This may be accomplished in the screen house of a water intake power plant simply by shutting off the water pumps. It is often not necessary to seal the intake channels of the screen house, although this may be done if desired. The conduit or hose may terminate a few inches above the bottom, with sulfite salt solution pouring in to treat preferably at least about the bottom 4 feet of the water in the screen house, which may be on the order of 30 to 40 feet deep by way of example.

Because sodium bisulfite solution is denser than water, a concentration gradient may be created in which the sulfite solution is concentrated preferably in the bottom 2 to 6 feet of water above the bed, with relatively very little sulfite ion diffusing upwardly. Thus under quiet-water conditions, only an amount of sulfite ion has to be added to provide the desired sulfite concentration in the bottom 2 to 6 feet or so of water, while the remaining water above the underwater bed may remain substantially free of sulfite ion, resulting in a substantial saving of ingredient.

It is also preferred for at least 0.5 part per million, and preferably on the order of 1 part per million, of dissolved cobalt salt such as cobalt chloride to be added to the sulfite salt, based on the weight of the sulfite salt, to serve as an oxidation catalyst.

Prererably one applies to a bottom zone of typically 4 to 6 feet depth at least twice the amount of sulfite salt which is theoretically needed to remove all free oxygen from the zone. This theoretical amount can be easily calculated by knowing the concentration of free oxygen in the water and the volume of water in the zone. Accordingly, by simple chemical calculation, the amount of sulfite ion to be added to the zone over the bed may be determined, knowing that each sulfite ion can take up one oxygen atom to form a sulfate ion.

The sulfite solution which is added to at least the bottom 2 feet of water above the bed may be premixed, and then added by a hose which extends from a tank of sulfite solution to the zone to which the sulfite is to be added. For example, a flexible hose may be manipulated by a diver to selectively add the sulfite to the bottom 3 to 6 feet of a screen house or other water inlet chamber of a water cooling unit for an electric utility or the like. Solid sulfite salt may also be placed in the zone to dissolve there, as desired.

Alternatively, permanent headers may be positioned in the bottom 1 or 2 feet of the zone, and permanent conduits may lead from a storage tank for the sulfite solution to the headers, which can distribute the sulfite solution throughout the bottom zone above the potential mussel beds.

The sulfite solution which is administered may contain, for example, from 300 to 900 pounds of solid sulfite salt, for example sodium metabisulfite, per 300 to 400 gallons of water.

In the drawings, FIG. 1 is a plan view of a screen house reservoir for providing a water supply for various water pumps of an electric utility.

Figure 2:
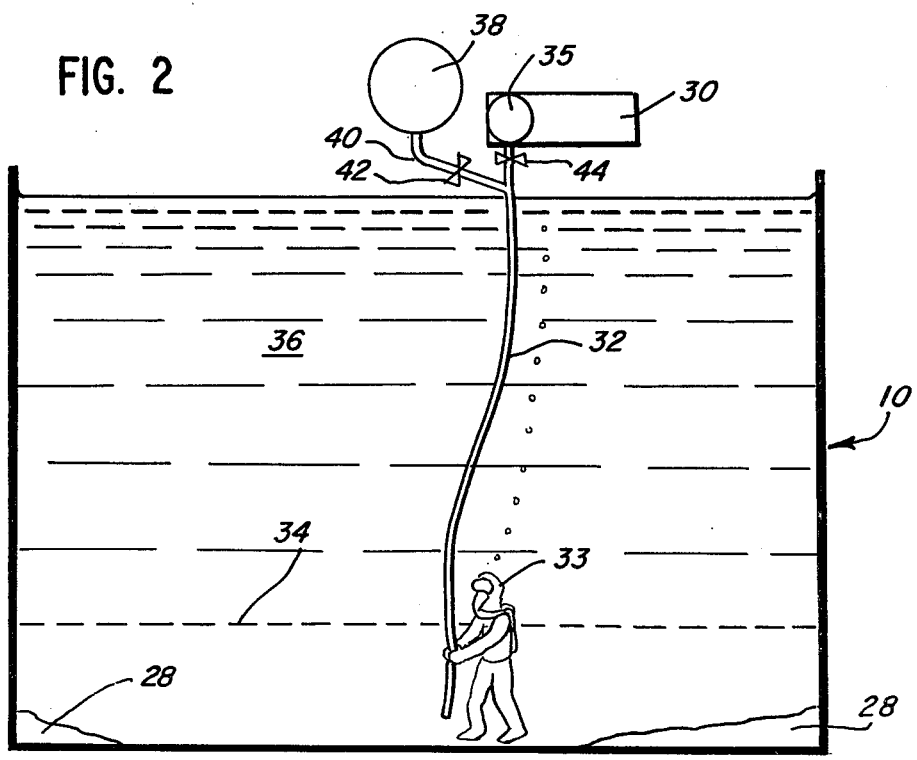

FIG. 2 is an elevational view of the interior of the screen house, shown partly schematically, showing a diver administering the sulfite solution to a zone comprising the bottom 4 feet or so of water in the screen house.

Referring to the drawings, screen house or crib house 10 comprises a large chamber 12 essentially surrounded with concrete walls 14 and having water intake channels 16 communicating with a river or a lake. Screens 18 are provided to filter out any large debris that might cause damage to the pumps, being separated by piers 20 to define the separate intake channels 16.

Circulating water pump intakes 22 provide water to condenser tubes of the heat exchangers of an electric power utility, which may be oil-fired, coal-fired, or nuclear, as the case may be.

Also, service water pumps 24 for general use of the utility are provided, while an emergency fire pump 26 is also provided, with all of the pumps extending substantially into the depth of the water in screen house 10. A typical water depth in the screen house is 36 to 40 feet, with the overall water volume capacity of the screen house being several hundreds of thousands of gallons of water, e.g. 500,000 gallons.

During the long term operation of screen house 10 for providing water to the various pumps 22, 24, 26, silt beds 28 collect in various areas, settling in the areas of the screen house 10 where the flow is relatively stagnant.

It has been found that the larvae of mussels, and particularly the Asiatic clam (Corbicula), a fresh water clam, flourish in these silt beds, with the result that the shells of dead clams are produced by the life cycle of the colony of clams. These shells plus live clams can be caught in the turbulence of the intake of the pumps, sucked into the pumps, and often become jammed in the condenser tubes, requiring dismantling of the condenser system to remove the clam shells on a periodic basis.

While it is possible to block channels 16 of the screen house, drain the screen house, and remove the silt periodically, it is an expensive and time-consuming operation. In accordance with this invention, an environmentally safe and inexpensive technique for eliminating the colonies of clams in silt beds 28 is utilized.

The various pumps 22, 24, 26 are simply shut off, which under most circumstances provides conditions in which at least the bottom currents in the water are essentially minimal.

About 200 pounds of preferably sodium metabisulfite may be placed in plastic bags, taken to the bottom of screen house 10 by a diver 33, and selectively dropped on the silt beds 28, for concentrated application.

Following this, water solution of preferably sodium metabisulfite, for example about 350 pounds of sodium metabisulfite per 300 to 400 gallons of water, is applied from storage tank 30 through siphon hose 32 to apply the sulfite solution to the bottom 4 to 6 feet of the water in crib house 10, indicated as zone 34 in FIG. 2. The sulfite solution is denser than the remainder of the water 36 and thus, when currents in the water are essentially minimal, the sulfite solution substantially remains in zone 34 where it is applied, adding to the sulfite concentration in the zone. Pump 35 may be used if desired. The diver 33 can slowly move about the zone 34, applying the solution through hose 32 until the desired amount of sulfite solution has been applied.

As stated before, it is preferable for the desired total amount of sulfite salt added to be at least about twice the necessary amount which is calculated as theoretically necessary to remove all dissolved oxygen from the water in zone 34. Because of the minimal current conditions in water 36, the oxygen from the upper levels of water migrates only very slowly into zone 34, thus maintaining anaerobic conditions in zone 34, while using an amount of sulfite salt which is capable of removing the oxygen from only a fraction of the total water present in crib house 10.

Under the anaerobic conditions provided by this invention, mussels and the other bottom dwelling creatures will be killed in typically 3 to 4 days.

The total amount of sulfite salt added to a typical 500,000 gallon capacity screen house may be about 600 to 900 pounds. Greater amounts are required in the winter due to the higher oxygen level in the water as well as the reduced metabolism of the clams and other bottom dwelling organisms. As stated above, cobalt chloride is preferably added at about 1 part per million of cobalt salt, based on the amount of sulfite salt present.

As described above, it is generally preferable to apply about a third of the sulfite salt prior to the solution addition step as shown in FIG. 2 in solid form to the bottom zone 34. Sodium metabisulfite may be sealed and carried to the bottom in 20 to 30 pound plastic bags, and then opened over the area where the clams are most abundant, and the silt the heaviest, to provide initial concentrated application of the sulfite salt.

In the above specific instance, an added 150 pounds of additional sodium metabisulfite in solution may be added during the subsequent hydrogen sulfide treatment, or, alternatively, prior to such addition if desired.

After the application of the sulfite salt, it is preferred to follow up with a second stage of treatment which comprises adding hydrogen sulfide gas to the anaerobic zone 34 created by the previous treatment. Hydrogen sulfide is not stable in aerated water. Thus any hydrogen sulfide that escapes into upper portions of the water level 36 will be oxidized, while the hydrogen sulfide which remains in the anaerobic zone 34, maintained by the presence of sulfite ion, will be stable for a period of days.

The hydrogen sulfide gas may be injected from tank 38 through an aspiration line 40 through hose 32 with valve 42 open and valve 44 closed for direct bubbling at typically 25 psig. of hydrogen sulfide gas through line 32 into zone 34. The gas is highly soluble in water, and the flow of gas is adjusted so that most of the dissolution of hydrogen sulfide gas takes place in zone 34. The gas can be bubbled through a $\frac{3}{4}$ inch inner diameter hose 32 for 15 minutes in each of 3 areas of screen house 10, for relatively uniform distribution of hydrogen sulfide in bottom zone 34.

Alternatively, the additional sulfite in solution mentioned above may flow from tank 30 through line 32, with valve 44 being opened, while valve 42 is also open so that the bottled hydrogen sulfide gas flows into the flowing sulfite solution at a pressure of preferably 30 to 35 psig., with the hose 32 being moved periodically about the bottom of the screen house 10 to distribute the hydrogen sulfide.

It is preferred for the diver 33 to be out of the tank during the hydrogen sulfide application process, because of the high toxicity of hydrogen sulfide. If the hydrogen sulfide is carried into the zone 34 by means of a liquid, it is preferred for the liquid to be the sulfite solution, which is devoid of free oxygen and thus the hydrogen sulfide remains stabilized.

Alternatively, bubble diffuser lines may be laid in the bottom of the screen house by a diver, with the gas being bubbled through the line at about 25 psig. for distribution of the hydrogen sulfide.

Generally for a typical 500,000 gallon screen house a total of about 30 to 60 pounds of hydrogen sulfide may be applied.

After this hydrogen sulfide application step, the water in the screen house is allowed to remain undisturbed, although it has been found that there is often no need to seal inlet channels 16 during the process. The period of waiting may vary from 2 to 4 days, depending upon the water temperature. At temperatures about 80° F. and with an application of hydrogen sulfide, only 36 hours may be required after treatment. During the colder months the full 4 days of treatment is often required. Improved kill levels are obtained with the hydrogen sulfide step.

Following this, an inspection may be made to determine the effectiveness of the treatment.

As a final, preferred step, the water in the bottom zone 34 may be detoxified prior to discharge. This may be done, for example, by bubbling compressed air through line 32 to the bottom of the screen house, while moving the line around or otherwise distributing the air, to oxidize any residual hydrogen sulfide and also sulfite ion, so that the remaining water solution is a sulfate solution, which is generally not very toxic or environmentally damaging.

The treated water can also be safely discharged using a single circulating water pump 22 or 24, to mix the water with the discharge of other generating units that are in service, until the water of anaerobic zone 34 is diluted with other water and is oxidized.

The method of this invention has proven effective, eliminating the numbers of condenser tubes which are plugged by clam shells, by preventing the growth of clams in silt beds 28 to a large enough size to cause a condenser problem. The method must be repeated periodically to prevent clams from growing to a size where they can cause such problems.

The annual cost of utilizing the method of this invention is much lower than other proposed control methods, and the above method can be environmentally safe.

It should be added that gas masks should be available at the site for the use of personnel in the event of a rupture of a hydrogen sulfide line or the tank, due to the toxicity of the gas.

As stated above, it may be desirable to install a permanent piping system at the bottom of screen house 10 to permit the distribution of sulfite solution and hydrogen sulfide, which would eliminate the need for a diver in the application. Also, header pipes incorporated into such a system could be connected as well to high pressure service water and pointed at the areas where silt and larval clams settle, to flush away silt and remove clam colonies on a regular basis from the screen house between the times when the treatment of this invention is required.

The above has been offered for illustrative purposes only, and is not intended to limit the scope of the invention of this application, which is as defined in the claims below.

That which is claimed is:

1. The method of eliminating mussels and the like from an underwater bed which comprises;
   applying to the zone of at least the bottom 2 feet of water above said bed sufficient water-soluble sulfite salt, having a substantially nontoxic cation, to substantially deplete dissolved oxygen in said zone, and maintaining said conditions until the desired mussel kill is obtained.

2. The method of claim 1 in which cation is sodium.

3. The method of claim 1 in which at least most of said sulfite salt is applied as a solution through a conduit directly into said zone under conditions in which currents in the water are essentially minimal, whereby a sulfite concentration gradient is created between said zone and the water above said zone.

4. The method of claim 1 in which at least about 0.5 part per million of dissolved cobalt salt, based on the sulfite salt, is added to said sulfite salt to serve as an oxidation catalyst.

5. The method of claim 1 in which said sulfite salt is selected from the group consisting of sodium bisulfite and sodium metabisulfite.

6. The method of claim 1 in which there is applied to said zone at least twice the amount of sulfite salt needed to remove all free oxygen from said zone.

7. The method of claim 1 in which said sulfite solution contains from 300 to 900 pounds of sodium metabisulfite per 300 to 400 gallons of water.

8. The method of eliminating mussels and the like from an underwater bed comprising a substantially enclosed area essentially free of water currents, which comprises:
   applying through a conduit directly into the zone of at least the bottom 2 feet of water sufficient water solution of a sodium sulfite salt to substantially deplete dissolved oxygen in said zone, to provide a sulfite concentration gradient between said zone and the water above said zone, and maintaining a sufficient concentration of said sulfite salt in the zone until the desired mussel kill is obtained.

9. The method of claim 8 in which there is applied to said zone at least twice the amount of sulfite salt theoretically needed to remove all free oxygen from said zone.

10. The method of claim 9 in which at least about 0.5 part per million of dissolved cobalt salt is added to said sulfite salt solution to serve as an oxidation catalyst.

11. The method of claim 10 in which said sulfite solution contains from 300 to 900 pounds of sodium metabisulfite per 300 to 400 gallons of water.

12. The method of claim 11 in which an added soluble sodium sulfite salt is added to said zone in solid form.

13. The method of eliminating mussels and the like from an underwater bed, which comprises:
   applying to the zone of at least the bottom 2 feet of water above said bed sufficient water-soluble sulfite salt having a substantially nontoxic cation to substantially deplete dissolved oxygen in said zone, and thereafter directly adding hydrogen sulfide to said zone, whereby the hydrogen sulfide is stabilized by the absence of dissolved oxygen in said zone, to increase the kill of mussels and the like in said underwater bed.

14. The method of claim 13 in which said cation is sodium.

15. The method of claim 13 in which said sulfite salt solution is applied through a conduit directly into said zone under conditions in which currents in the water are essentially minimal, whereby a sulfite concentration gradient is created between said zone and the water above said zone.

16. The method of claim 13 in which at least about 0.5 part per million of dissolved cobalt salt, based on the weight of said sulfite salt, is added to said sulfite salt to serve as an oxidation catalyst.

17. The method of claim 13 in which said sulfite salt is selected from the group consisting of sodium bisulfite and sodium metabisulfite.

18. The method of claim 13 in which there is applied to said zone at least twice the amount of sulfite salt theoretically needed to remove all free oxygen from said zone.

19. The method of claim 13 in which at least most of said sulfite salt is added as a water solution.

20. The method of claim 19 in which said sulfite solution contains from 300 to 900 pounds of sodium metabisulfite per 300 to 400 gallons of water.

21. The method of claim 13 in which said hydrogen sulfide is added as a gas through a conduit extending into said zone.

22. The method of claim 13 in which said hydrogen sulfide is added to a water solution of sulfite salt after initial amounts of said sulfite salt have been added to the zone to substantially deplete the dissolved oxygen, and the hydrogen sulfide containing water solution is then also added to said zone.

23. The method of claim 13 in which 30 to 60 pounds of hydrogen sulfide are added.

24. The method of eliminating mussels and the like from an underwater bed, which comprises:

applying to the zone of at least the bottom 2 feet of water above said bed sufficient water solution of a sulfite salt selected from the group consisting of sodium bisulfite and sodium metabisulfite, at least some of said sulfite salt being applied as a solution directy through a conduit into said zone under conditions in which currents in the water are essentially minimal, whereby the dissolved oxygen in said zone is substantially depleted and a sulfite concentration gradient is created between said zone and the water above said zone, and thereafter hydrogen sulfide is added to said zone, said hydrogen sulfide being applied directly through a conduit into said zone under conditions in which currents in the water are essentially minimal, and maintaining a concentration of hydrogen sulfide under oxygen depleted conditions in said zone sufficient to obtain the desired mussel kill.

25. The method of claim 24 in which at least about 0.5 part per million of dissolved cobalt salt is added to said sulfite salt to serve as an oxidation catalyst.

26. The method of claim 25 in which there is applied to said zone at least twice the amount of sulfite salt theoretically needed to remove all free oxygen from said zone.

27. The method of claim 26 in which said hydrogen sulfide is added as a gas through a conduit extending into said zone.

28. The method of claim 27 in which said hydrogen sulfide is added to said water solution of sulfite salt after initial amounts of said water solution of sulfite salt have been added to the zone to substantially deplete the dissolved oxygen, and the hydrogen sulfide containing water solution is then also added to said zone.

29. The method of claim 28 in which, after the desired mussel kill is obtained, said zone is aerated by bubbling air therethrough, to oxidize any remaining hydrogen sulfide.

* * * * *